(12) United States Patent
Botros et al.

(10) Patent No.: US 9,744,356 B2
(45) Date of Patent: *Aug. 29, 2017

(54) AUTOMATIC DETERMINATION OF THE THRESHOLD OF AN EVOKED NEURAL RESPONSE

(71) Applicant: Cochlear Limited, Macquarie University, NSW (AU)

(72) Inventors: Andrew Botros, Maroubra (AU); Matthijs Killian, Mechelen (BE); Bastiaan van Dijk, Deurne (BE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/590,589

(22) Filed: Jan. 6, 2015

(65) Prior Publication Data
US 2015/0126897 A1 May 7, 2015

Related U.S. Application Data

(63) Continuation of application No. 10/569,054, filed as application No. PCT/US2005/021207 on Jun. 15, 2005, now Pat. No. 8,965,520.

(30) Foreign Application Priority Data

Jun. 15, 2004 (AU) ............................... 2004903254

(51) Int. Cl.
*A61N 1/00* (2006.01)
*A61N 1/36* (2006.01)
(Continued)

(52) U.S. Cl.
CPC ...... *A61N 1/36032* (2013.01); *A61B 5/04001* (2013.01); *A61B 5/7264* (2013.01);
(Continued)

(58) Field of Classification Search
None
See application file for complete search history.

(56) References Cited

U.S. PATENT DOCUMENTS 227,118 A   5/1880 Man
452,003 A   5/1891 Lipe
(Continued)

FOREIGN PATENT DOCUMENTS

EP   0282336      9/1988
EP   0282338 A2   9/1988
(Continued)

OTHER PUBLICATIONS

Japanese Office Action for Japanese Application No. 2007-516701 and its English translation (6 pages).
(Continued)

*Primary Examiner* — Christopher D Koharski
*Assistant Examiner* — Elizabeth K So
(74) *Attorney, Agent, or Firm* — Edell, Shapiro & Finnan, LLC

(57) ABSTRACT

Techniques for automatically analyzing neural activity within a target neural region. In one example, electrical stimulation is applied to the target neural region at an initial current level that approximates a typical threshold-Neural Response Telemetry (NRT) level. An NRT measurement of neural activity within the target neural region in response to the stimulation is recorded. A machine-learned expert system, which is configured with a decision tree that includes at least two levels of nodes which consider parameters relating to the NRT measurement, respectively, is utilized to predict, based on one or more features of the neural activity, whether the NRT measurement includes a neural response or does not include a neural response.

12 Claims, 13 Drawing Sheets

(51) Int. Cl.
  *A61B 5/04* (2006.01)
  *A61B 5/00* (2006.01)
  *A61N 1/05* (2006.01)

(52) U.S. Cl.
  CPC .......... *A61B 5/7275* (2013.01); *A61B 5/7282* (2013.01); *A61N 1/00* (2013.01); *A61N 1/0541* (2013.01)

(56) References Cited

U.S. PATENT DOCUMENTS

| | | |
|---|---|---|
| 3,043,000 A | 7/1962 | Hatfield |
| D227,118 S | 6/1973 | Muraoka |
| 3,771,685 A | 11/1973 | Micallef |
| 4,003,521 A | 1/1977 | Hess |
| 4,114,627 A | 9/1978 | Lewyn et al. |
| 4,226,164 A | 10/1980 | Carter |
| 4,240,428 A | 12/1980 | Akhavi |
| 4,305,396 A | 12/1981 | Wittkampf et al. |
| 4,343,312 A | 8/1982 | Cals et al. |
| D267,541 S | 1/1983 | Kanemitsu |
| 4,373,531 A | 2/1983 | Wittkampf et al. |
| 4,414,701 A | 11/1983 | Johnson |
| 4,532,930 A | 8/1985 | Crosby et al. |
| 4,543,956 A | 10/1985 | Herscovici |
| 4,610,621 A | 9/1986 | Taber et al. |
| 4,611,596 A | 9/1986 | Wasserman |
| 4,731,718 A | 3/1988 | Sheu |
| 4,736,751 A | 4/1988 | Gevins et al. |
| 4,895,152 A | 1/1990 | Callaghan et al. |
| 4,917,504 A | 4/1990 | Scott et al. |
| 4,920,679 A | 5/1990 | Sarles et al. |
| 4,941,179 A | 7/1990 | Bergenstoff et al. |
| 5,014,592 A | 5/1991 | Zweig et al. |
| 5,016,280 A | 5/1991 | Engebretson et al. |
| 5,034,918 A | 7/1991 | Jeong |
| 5,095,904 A | 3/1992 | Seligman et al. |
| 5,172,690 A | 12/1992 | Nappholz et al. |
| 5,271,397 A | 12/1993 | Seligman et al. |
| 5,277,694 A | 1/1994 | Leysieffer et al. |
| 5,278,994 A | 1/1994 | Black et al. |
| D348,067 S | 6/1994 | Lucey et al. |
| 5,611,350 A | 3/1997 | John |
| 5,626,629 A | 5/1997 | Faltys et al. |
| 5,674,264 A | 10/1997 | Carter et al. |
| 5,748,651 A | 5/1998 | Sheynblat |
| 5,758,651 A | 6/1998 | Nygard et al. |
| 5,775,652 A | 7/1998 | Crawshaw et al. |
| 5,785,477 A | 7/1998 | McGuffey et al. |
| 5,792,751 A | 8/1998 | Ledley et al. |
| 5,895,416 A | 4/1999 | Barreras, Sr. et al. |
| 5,941,906 A | 8/1999 | Barreras, Sr. et al. |
| 5,963,904 A | 10/1999 | Lee et al. |
| 5,971,334 A | 10/1999 | Crawshaw et al. |
| 5,999,856 A | 12/1999 | Kennedy |
| 6,002,966 A | 12/1999 | Loeb et al. |
| 6,035,001 A | 3/2000 | Eklund et al. |
| 6,043,221 A | 3/2000 | Magal et al. |
| 6,044,162 A | 3/2000 | Mead et al. |
| 6,073,973 A | 6/2000 | Boscaljon et al. |
| 6,121,235 A | 9/2000 | Gao |
| 6,129,685 A | 10/2000 | Howard, III |
| 6,151,400 A | 11/2000 | Seligman |
| 6,157,861 A | 12/2000 | Faltys et al. |
| 6,175,767 B1 | 1/2001 | Doyle, Sr. |
| 6,205,360 B1 | 3/2001 | Carter et al. |
| 6,221,908 B1 | 4/2001 | Kilgard et al. |
| 6,249,704 B1 | 6/2001 | Maltan et al. |
| 6,287,328 B1 | 9/2001 | Snyder et al. |
| 6,289,247 B1 | 9/2001 | Faltys et al. |
| 6,304,787 B1 | 10/2001 | Kuzma et al. |
| 6,331,537 B1 | 12/2001 | Hamilton et al. |
| 6,428,484 B1 | 8/2002 | Battmer et al. |
| 6,429,191 B1 | 8/2002 | Gao |
| 6,429,196 B1 | 8/2002 | Gao |
| 6,430,402 B1 | 8/2002 | Agahi-Kesheh |
| 6,463,328 B1 | 10/2002 | John |
| 6,537,200 B2 | 3/2003 | Leysieffer et al. |
| 6,565,503 B2 | 5/2003 | Leysieffer et al. |
| 6,571,676 B1 | 6/2003 | Folsom et al. |
| 6,575,894 B2 | 6/2003 | Leysieffer et al. |
| 6,600,955 B1 | 7/2003 | Zierhofer |
| 6,649,621 B2 | 11/2003 | Kopke et al. |
| 6,671,559 B2 | 12/2003 | Goldsmith et al. |
| 6,697,674 B2 | 2/2004 | Leysieffer |
| 6,731,767 B1 | 5/2004 | Blamey et al. |
| 6,751,505 B1 | 6/2004 | Van Den Honert et al. |
| 6,892,092 B2 | 5/2005 | Palreddy et al. |
| 6,907,130 B1 | 6/2005 | Rubinstein et al. |
| 6,915,166 B1 | 7/2005 | Stecker et al. |
| 7,043,303 B1 | 5/2006 | Overstreet |
| 7,801,617 B2 | 9/2010 | Dijk et al. |
| 8,019,432 B2 | 9/2011 | Dijk et al. |
| 2001/0049466 A1 | 12/2001 | Leysieffer et al. |
| 2002/0026091 A1 | 2/2002 | Leysieffer |
| 2002/0115706 A1 | 8/2002 | Ylikoski et al. |
| 2002/0176859 A1 | 11/2002 | Gao |
| 2003/0171787 A1 | 9/2003 | Money et al. |
| 2004/0082980 A1 | 4/2004 | Mouine et al. |
| 2004/0098063 A1 | 5/2004 | Goetz |
| 2004/0247570 A1 | 12/2004 | Miller et al. |
| 2005/0004627 A1 | 1/2005 | Gibson et al. |
| 2005/0015133 A1 | 1/2005 | Ibrahim et al. |
| 2005/0033377 A1 | 2/2005 | Milojevic et al. |
| 2005/0101878 A1 | 5/2005 | Daly et al. |
| 2005/0107845 A1 | 5/2005 | Wakefield et al. |
| 2005/0171579 A1 | 8/2005 | Tasche et al. |
| 2005/0245991 A1 | 11/2005 | Faltys et al. |
| 2005/0256560 A1 | 11/2005 | Lenarz et al. |
| 2006/0171922 A1 | 8/2006 | Federoff et al. |
| 2006/0178711 A1 | 8/2006 | Patrick et al. |
| 2006/0235332 A1 | 10/2006 | Smoorenburg |
| 2007/0084995 A1 | 4/2007 | Newton et al. |
| 2007/0112395 A1 | 5/2007 | Dijk et al. |
| 2007/0255344 A1 | 11/2007 | Van Dijk |
| 2008/0221640 A1* | 9/2008 | Overstreet ......... A61N 1/37247 607/48 |
| 2009/0043359 A1 | 2/2009 | Smoorenburg |
| 2009/0076569 A1 | 3/2009 | Busby et al. |
| 2011/0015700 A1 | 1/2011 | Dijk et al. |
| 2011/0082521 A1 | 4/2011 | Botros et al. |

FOREIGN PATENT DOCUMENTS

| | | |
|---|---|---|
| EP | 0836363 | 4/1998 |
| EP | 1765459 A | 3/2007 |
| GB | 414579 | 8/1934 |
| GB | 2266045 A | 10/1993 |
| JP | 63226340 | 9/1988 |
| JP | 2992080 | 10/1999 |
| JP | 2000350709 | 12/2000 |
| JP | 2008506422 | 3/2008 |
| WO | 9210134 | 6/1992 |
| WO | 9324176 | 12/1993 |
| WO | 9414376 | 7/1994 |
| WO | 9501709 | 1/1995 |
| WO | 9612383 | 4/1996 |
| WO | 9709863 | 3/1997 |
| WO | 9748447 | 12/1997 |
| WO | 0052963 | 9/2000 |
| WO | 0076436 | 12/2000 |
| WO | 0113991 | 3/2001 |
| WO | 0141867 | 6/2001 |
| WO | 0143818 | 6/2001 |
| WO | 0156521 A1 | 8/2001 |
| WO | 02082982 | 10/2002 |
| WO | 03039660 | 5/2003 |
| WO | 03070322 | 8/2003 |
| WO | 2004004412 | 1/2004 |
| WO | 2004021885 | 3/2004 |
| WO | 2004080532 A1 | 9/2004 |
| WO | 2005006808 | 1/2005 |

(56) References Cited

FOREIGN PATENT DOCUMENTS

| WO | 2005122887 | 12/2005 |
|---|---|---|
| WO | 2009124035 | 10/2009 |

OTHER PUBLICATIONS

Mitchell et al., "Effects of chronic high-rate electrical stimulation on the cochlea and eight nerve in the deafened guinea pig", Hearing Research, Elsevier Science Publishers, Amsterdam, NL, vol. 105, No. 1-2, Mar. 1997, pp. 30-43.
International Search Report & Written Opinion; International Application No. PCT/US06/02793 mailed May 10, 2007.
Written Opinion; International Application No. PCT/AU02/01537 mailed Jun. 23, 2003.
International Preliminary Examination Report, International Application No. PCT/AU02/01537 mailed Feb. 13, 2004.
Abbas et al., "Electrically Evoked Compound Action Potentials Recorded from Subjects Who Use the Nucleus CI24M Device," Ann. Otol. Rhinol. Laryngol. Suppl.; Dec. 2000; 185: pp. 6-9.
Australian Examiner's First Report for Patent Application No. 2005254100, dated Dec. 17, 2009.
Austrian First Office Action (English Translation) for Austrian Official file No. 3B A 9165/2003-1, related to PCT/AU2003/000804, dated Mar. 20, 2007.
Baumgarte, et al., "A Nonlinear Psychoacoustic Model Applied to the ISO MPEG Layer 3 Coder," Proc. 99th Cony. Aud. Eng. Soc., New York, NY, Oct. 1995, preprint 4087.
Cohen et al., "Spatial Spread of Neural Excitation in Cochlear Implant Recipients: Comparison of Improved ECAP Method and Psychophysical Forward Masking," Hearing Research, 179 (2003), pp. 72-87.
Cohen et al., "Spatial Spread of Neural Excitation: Comparison of Compound Action Potential and Forward-Masking Data in Cochlear Implant Recipients," International Journal of Audiology 2004, 43, pp. 346-355.
Edler, et al., "ASAC-Analysis/Synthesis Audio Codec for Very Low Bit Rates," Proc. 100th Cony. Aud. Eng. Soc., May 1996, preprint 4179.
European Search Report (Annex), EP 01 95 9971, dated Aug. 2, 2005.
Hartmann et al., "Evoked Potentials from the Auditory Nerve Following Sinusoidal Electrical Stimulation of the Cochlea: New Possibilities for Preoperative Testing in Cochlear—Implant Candidates?" Acta Otoloaryngol (Stockh) 1994, 114, pp. 495-500.
International Preliminary Examination Report for PCT/AU2003/000804, dated Dec. 20, 2006.
International Preliminary Examination Report for PCT/FR2003/000577, dated May 7, 2004 (English translation).
International Preliminary Examination Report for PCT/AU02/00500, dated Feb. 12, 2003.
International Preliminary Report on Patentability for PCT/US2005/021207, dated Dec. 20, 2006.
International Search Report for PCT/AU2003/000804, dated Aug. 26, 2003.
International Search Report PCT/FR2003/00577, dated Jul. 4, 2003 (English translation).
International Search Report for PCT/US2009/038932, dated Jun. 5, 2009.
International Search Report for PCT/AU01/01032, dated Oct. 5, 2001.
International Search Report for PCT/AU02/00500, dated Jun. 26, 2002.
International Search Report for PCT/US2005/021207 dated Feb. 8, 2006.
Miller et al., "An Improved Method of Reducing Stimulus Artifact in the Electrically Evoked Whole-Nerve Potential," Ear & Hearing, vol. 21, No. 4, Aug. 2000, pp. 280-290.
Riedmiller et al., "A Direct Adaptive Method for Faster Backpropagation Learning: The RPROP Algorithm," Proceedings of the International IEEE Conference on Neural Networks—1993, vol. 1, Mar. 28 -Apr. 1, 1993, pp. 586-591.
Supplementary Partial European Search Report, EP 02 71 7863 dated Oct. 18, 2005.
Written Opinion for PCT/AU2003/00804, dated Oct. 16, 2003.
Written Opinion for PCT/US2009/038932, dated Jun. 5, 2009.
Written Opinion for PCT/US2005/021207 dated Feb. 8, 2006.
Brown et al., The Relationship between EAP and EABR Thresholds and Levels Used to Program the Nucleus 24 Speech Processor: Data from Adults, Ear Hear vol. 21(2), Apr. 2000, pp. 151-163.
Charasse et al., Automatic Analysis of Auditory Nerve Electrically Evoked Compound Action Potential with an Artificial Neural Network, Artificial Intelligence in Medicine, Mar. 3, 2004, pp. 221-229.
Charasse et al., "Comparison of Two Different Methods to Automatically Classify Auditory Nerve Responses Recorded with NRT System," Acta Acustica United with Acustica, vol. 90, Jan. 22, 2004, pp. 512-519.
Delgado et al., "Automated Auditory Brainstem Response Interpretation," IEEE Engineering in Medical and Biology, May 1994, pp. 227-237.
Franck et al., "Estimation of Psychophysical Levels Using the Electrically Evoked Compound Action Potential Measured with the Neural Response Telemetry Capabilities of Cochlear Corporation's CI24M Device," Ear & Hearing, 2001, pp. 289-299.
Hughes et al., "Comparison of EAP Thresholds with MAP Levels in the Nucleus 24 Cochlear Implant: Data from Children," Ear and Hearing, vol. 21(2), Apr. 2000, pp. 164-174.
Nicolai et al., Performance of Automatic Recognition Algorithms in Nucleus Neural Response Telemetry (NRT). Cochlear, Conference on Implantable Auditory Prostheses (Asilomar), 2003, one page total.
Seyle et al., "Speech Perception Using Maps Based on Neural Response Telemetry Measures," Ear & Hearing, pp. 72S-79S, 2002.
Bas van Dijk et al., "Development of a Prototype Fully-Automated Intra-Operative ECAP Recording Tool, Using NRT v3." Conference on Implantable Auditory Prostheses (Asilomar), 2003, 7 pages total.
Vannier et al., "Objective Detection of Brainstem Auditory Evoked Potentials with a Priori Information from Higher Presentation Levels," Artificial Intelligence in Medicine, Feb. 21, 2002, pp. 283-301.
Abbas et al., "Summary of Results Using the Nucleus CI24M Implant to Record the Electrically Evoked Compound Action Potential," Eat and Hearing, vol. 20(1), Feb. 1999, pp. 45-59.
Brown et al., "Electrically Evoked Whole-Nerve Action Potentials: Data from Human Cochlear Implant Users," Journal of Acoustical Society of America, Sep. 1990, pp. 1385-1391.
Dillier et al., "Measurement of the Electrically Evoked Compound Action Potential via a Neural Response Telemetry System," Annals of Otology, Rhinology & Laryngology, vol. 111, No. 5, May 2002, pp. 407-414.
Franck, "A model of a Nucleus 24 Cochlear Implant Fitting Protocol Based on the Electrically Evoked Whole Nerve Action Potential," Ear & Hearing, 2002, pp. 67S-71S.
Lai et al., "A Simple Two-Component Model of the Electrically Evoked Compound Action Potential in the Human Cochlea," Audiology & Neuro—Otology, Apr. 4, 2000, pp. 333-345.
Smoorenburg et al., "Speech Perception in Nucleus C124M Cochlear Implant Users with Processor Settings Based on Electrically Evoked Compound Action Action Potential Thresholds," Audiology & Neuro—Otology, Feb. 9, 2002, pp. 335-347.
Thai-Van et al., "Modeling the Relationship Between Psychophysical Perception and Electrically Evoked Compound Action Potential Threshold in Young Cochlear Implant Recipients: Clinical Implications for Fitting," Clinical Neurophysiology 115, 2004, pp. 2811-2824.
European Application No. 02717863, Supplementary Partial Search Report mailed on Oct. 18, 2005, 5 Pages.
Australian Application No. 2005254100, Office Action mailed on Feb. 22, 2011, 3 Pages.
International Preliminary Examination Report for PCT/AU01/01032, dated Apr. 10, 2002.

* cited by examiner

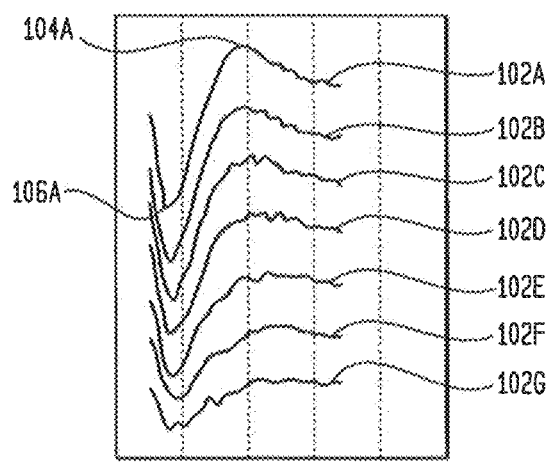
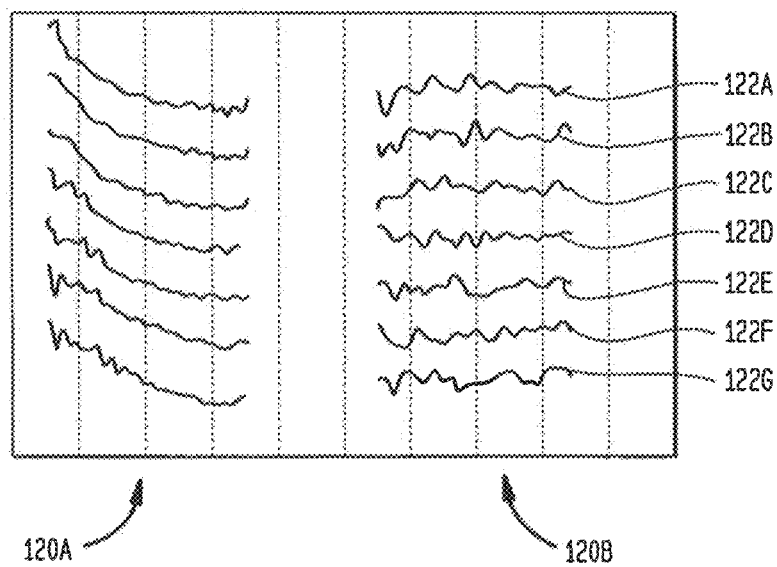

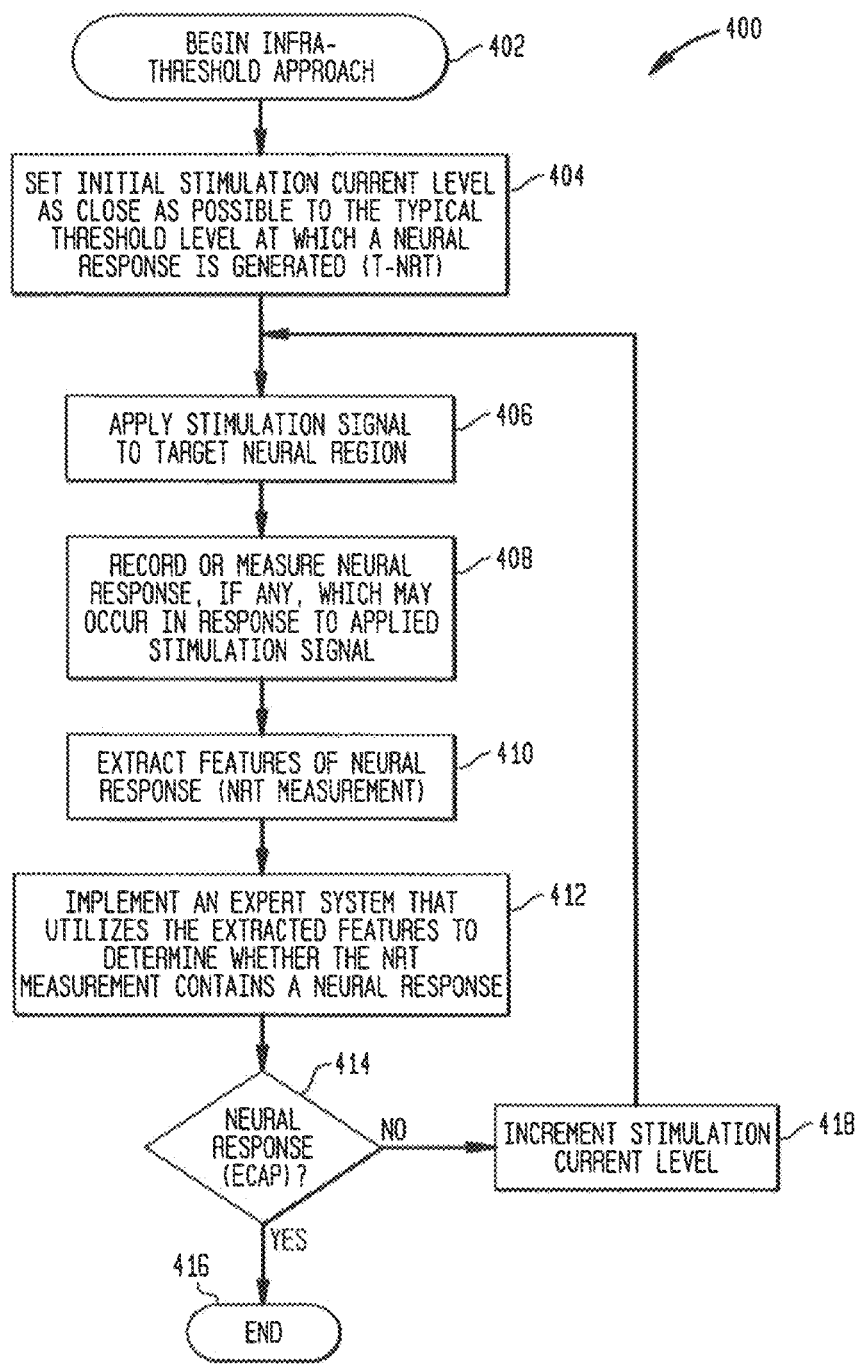

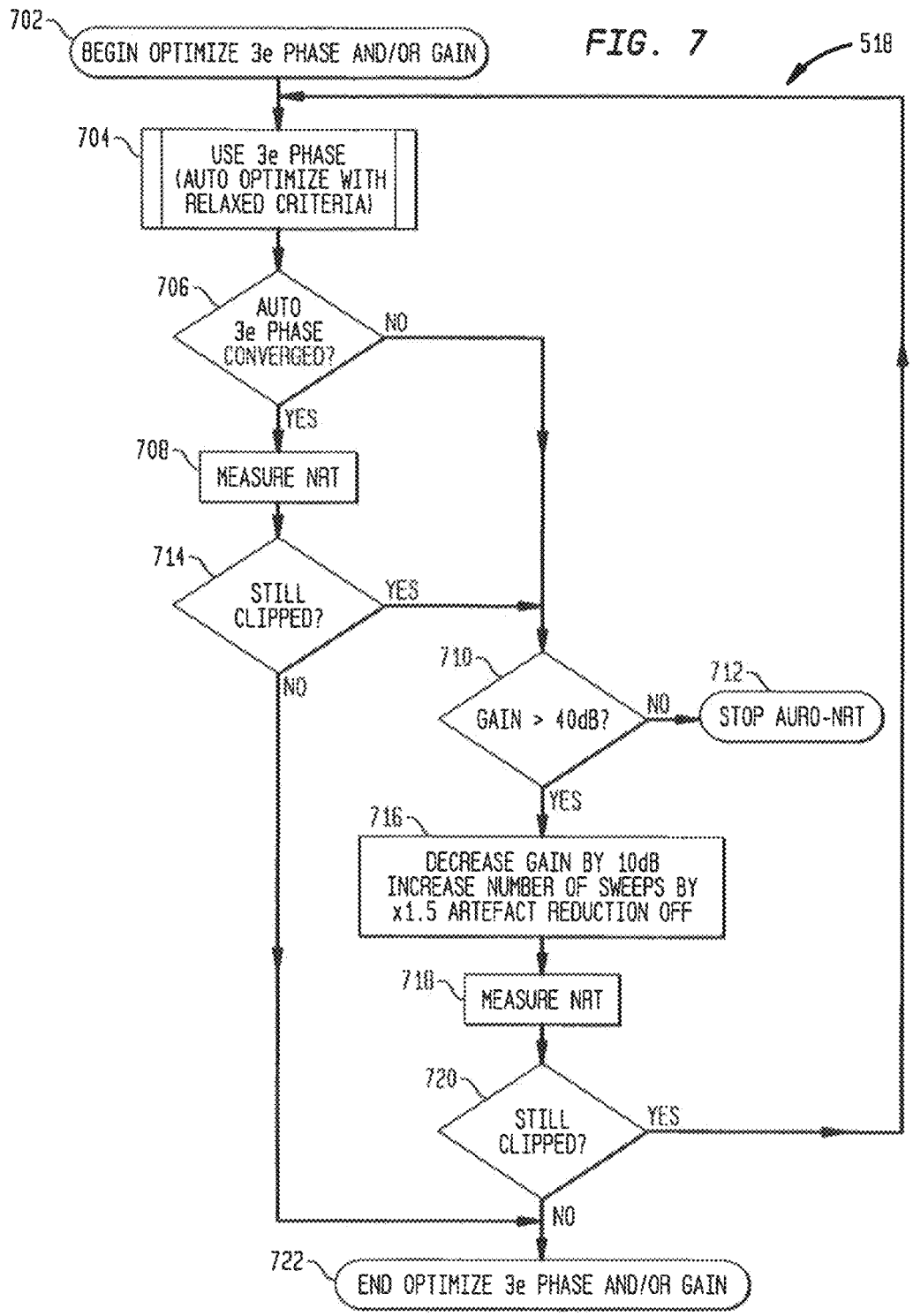

AUTOMATIC DETERMINATION OF THE THRESHOLD OF AN EVOKED NEURAL RESPONSE

CROSS-REFERENCE TO RELATED APPLICATIONS

This application is a continuation application of U.S. patent application Ser. No. 10/596,054 (now U.S. Pat. No. 8,965,520), filed on Feb. 22, 2006, which is a national stage application under 35 USC §371(c) of PCT Application No. PCT/US2005/21207, entitled "Automatic Determination of the Threshold of an Evoked Neural Response," filed Jun. 15, 2005, which claims the priority of Australian Patent No. 2004903254 entitled, "Method and System for Measurement of Neural Response," filed Jun. 15, 2004. The above applications are hereby incorporated by reference herein in their entireties.

The present application makes reference to the following patents and patent applications: U.S. Pat. Nos. 4,532,930, 5,758,651, 6,537,200, 6,565,503, 6,575,894 and 6,697,674, WO 2002/082982 and WO 2004/021885, which are hereby incorporated by reference herein in their entirety.

BACKGROUND

Field of the Invention

The present invention relates generally to the measurement of a neural response evoked by electrical stimulation and, more particularly, to the automatic measurement of an evoked neural response.

Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional auditory prostheses commonly referred to as hearing aids, which amplify sound so that acoustic information can reach the cochlea.

In many people who are profoundly deaf, however, the reason for their deafness is sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids due to the damage to or absence of the mechanism for naturally generating nerve impulses from sound.

It is for this purpose that another type of auditory prosthesis, a cochlear implant, has been developed. These types of auditory prostheses bypass the hair cells in the cochlea, directly delivering electrical stimulation to the auditory nerve fibers via an implanted electrode assembly. This enables the brain to perceive a hearing sensation resembling the natural hearing sensation normally delivered to the auditory nerve.

Cochlear implants have traditionally comprised an external speech processor unit worn on the body of the recipient and a receiver/stimulator unit implanted in the mastoid bone of the recipient. The external speech processor detects external sound and converts the detected sound into a coded signal through an appropriate speech processing strategy. The coded signal is sent to the implanted receiver/stimulator unit via a transcutaneous link. The receiver/stimulator unit processes the coded signal to generate a series of stimulation sequences which are then applied directly to the auditory nerve via a series-arrangement or an array of electrodes positioned within the cochlea.

More recently, the external speech processor and implanted stimulator unit may be combined to produce a totally implantable cochlear implant capable of operating, at least for a period of time, without the need for an external device. In such an implant, a microphone would be implanted within the body of the recipient, for example in the ear canal or within the stimulator unit. Detected sound is directly processed by a speech processor within the stimulator unit, with the subsequent stimulation signals delivered without the need for any transcutaneous transmission of signals.

Generally, there is a need to obtain data from the implanted components of a cochlear implant. Such data collection enables detection and confirmation of the normal operation of the device, and allows stimulation parameters to be optimized to suit the needs of individual recipients. This includes data relating to the response of the auditory nerve to stimulation, which is of particular relevance to the present invention. Thus, regardless of the particular configuration, cochlear implants generally have the capability to communicate with an external device such as for program upgrades and/or implant interrogation, and to read and/or alter the operating parameters of the device.

Determining the response of an auditory nerve to stimulation has been addressed with limited success in conventional systems. Typically, following the surgical implantation of a cochlear implant, the implant is fitted or customized to conform to the specific recipient demands. This involves the collection and determination of patient-specific parameters such as threshold levels (T levels) and maximum comfort levels (C levels) for each stimulation channel. Essentially, the procedure is performed manually by applying stimulation pulses for each channel and receiving an indication from the implant recipient as to the level and comfort of the resulting sound. For implants with a large number of channels for stimulation, this process is quite time consuming and rather subjective as it relies heavily on the recipient's subjective impression of the stimulation rather than any objective measurement.

This approach is further limited in the case of children and prelingually or congenitally deaf patients who are unable to supply an accurate impression of the resultant hearing sensation, and hence fitting of the implant may be suboptimal. In such cases an incorrectly-fitted cochlear implant may result in the recipient not receiving optimum benefit from the implant, and in the cases of children, may directly hamper the speech and hearing development of the child. Therefore, there is a need to obtain objective measurements of patient-specific data, especially in cases where an accurate subjective measurement is not possible.

One proposed method of interrogating the performance of an implanted cochlear implant and making objective measurements of patient-specific data such as T and C levels is to directly measure the response of the auditory nerve to an electrical stimulus. The direct measurement of neural responses, commonly referred to as Electrically-evoked Compound Action Potentials (ECAPs) in the context of cochlear implants, provides an objective measurement of the response of the nerves to electrical stimulus. Following electrical stimulation, the neural response is caused by the superposition of single neural responses at the outside of the axon membranes. The measured neural response is transmitted to an externally-located system, typically via a telemetry system. Such Neural Response Telemetry (NRT) provides measurements of the ECAPs from within the cochlea in response to various stimulations. The measurements taken to determine whether a neural response or ECAPs has occurred are referred to herein by the common vernacular NRT measurements. Generally, the neural response resulting from a stimulus presented at one electrode is measured at a neighboring electrode, although this need not be the case.

A sequence 100 of NRT measurements 102 is shown in FIG. 1A. Sequence 100 contains seven NRT measurements 102A-102G which display a good neural response. Each NRT measurement waveform 102A-102G comprises a clear negative peak (N1) 104 and positive peak (P1) 106. Only one positive and negative peak is shown in FIG. 1A for clarity. As used herein, a "good" neural response is one which approximates a true neural response to an applied stimulus current.

An NRT measurement waveform may have a partial N1 peak, no P1 peak or a double positive peak P1 and P2 and still represent a good neural response. The measurement waveforms 102 toward the top of the graph depicted in FIG. 1A (measurement waveforms 102A, 102B, for example) indicates a stronger neural response to a relatively large neural stimulus, while the measurement waveforms toward the bottom of the graph (measurement waveforms 102F and 102G, for example) indicate a weaker neural response with reduced neural stimuli strengths.

Two sequences 120A and 120B of seven (7) NRT measurements 122A-122G that display the absence of a neural response are shown in FIG. 1B. In the left-hand sequence 120A, stimulus artifact and/or noise are observed. The stimulus artifact may give the impression of artificial peaks which may be interpreted as a neural response to a previously applied stimulus signal. In right-hand sequence 120B, noise is observed.

Distinguishing between measurements that display a neural response such as those of FIG. 1A, and measurements which do not display a neural response such as those of FIG. 1B, is an important aspect of performing NRT measurements. This task can be extremely difficult, for instance when the combination of stimulus artifact and noise gives the appearance of a weak neural response.

In particular, the minimum stimulus current level required to evoke a neural response at a given electrode is referred to herein as the threshold NRT level, or T-NRT. In general, T-NRT profiles are correlated with MAP T and C profiles, and thus T-NRT levels can be used as a guide for MAP fitting. Accordingly, accurate determination of T-NRT values for each electrode and for each recipient is highly desirable.

One conventional approach to determine T-NRT values is the Amplitude Growth Function (AGF) method. The AGF method is based on the premise that the peak-to-peak amplitude of a neural response increases linearly with stimulus current level. It should be appreciated, however, that the relationship is more accurately defined by a sigmoidal function. By obtaining the value at different stimulus current levels, a regression line may be drawn through these measurement points and extrapolated to the point at which the peak-to-peak amplitude becomes zero, thus indicating the threshold stimulus level.

For example, FIG. 2 illustrates a typical, non-linear, measurement set of peak-to-peak amplitude (in microvolts) vs. current level (in digitized current level units). As is well known in the art, there is a one-to-one exponential relationship between the unit of current level and the conventional unit of current (the ampere). In one embodiment, the current level scale is from 0 to 255 with each unit representing an increasingly lager quantity of amperes. This single set of measurements 200 (only one of which is referenced in FIG. 2 for ease of illustration) can be fitted with a number of regression lines 202A, 202B, and 202C, yielding possible T-NRT values of 125, 135 and 148 current level units, a variation of over 18%. This is because AGF is observer-dependent when selecting the measurement points to include in regression.

In addition, the AGF approach requires a significant number of NRT measurements above the threshold to enable a regression line to be determined. Such measurements may be beyond the recipient's loudest acceptable or comfort level, and thus the ability to postoperatively obtain such measurements is limited. Additionally, such measurements do not yield a simple linear relationship, and typically various regression lines can be determined resulting in significantly different T-NRT levels from a given measurement set.

Visual detection of T-NRT levels is a more fundamental conventional approach. NRT measurements of increasing stimulus level are performed until the stimulus level at which a neural response is detected, at which point the T-NRT level is defined as the stimulus level. Visual detection depends critically on the acuity of the observer to distinguish between neural responses and artifact or noise. Visual detection of threshold is also observer-dependent.

The presence of stimulus artifacts and noise in measurements of an evoked neural response can lead to an incorrect determination of whether a neural response, or ECAP, has occurred in the above conventional systems. Accordingly, there is a need to objectively and accurately detect T-NRT thresholds to facilitate neural response determinations.

Indeed, there is a need to accurately measure the response of nerves to electrical stimulation in stimulating medical devices that deliver electrical stimulation to other neural regions of a recipient such as the central nervous system (including the brain and spinal cord), as well as the peripheral nervous system (including the autonomic and sensory-somatic nervous systems). Thus, the accurate measurement of a neural response may provide a useful objective measurement of the effectiveness of the stimulation in many applications.

SUMMARY

In one aspect of the invention, a method is disclosed. The method comprises: applying electrical stimulation to a target neural region at an initial current level that approximates a typical threshold-Neural Response Telemetry (NRT) level; recording an NRT measurement of neural activity within the target neural region in response to the stimulation; and utilizing a machine-learned expert system configured with a decision tree that includes at least two levels of nodes which consider parameters relating to the NRT measurement, respectively, so as to predict, based on one or more features of the neural activity, whether the NRT measurement includes a neural response or does not include a neural response.

In another aspect of the invention, a system is disclosed. The system is communicably coupled to a cochlear implant implanted in a recipient and comprises one or more processors configured to: cause the cochlear implant to apply electrical stimulation to a target neural region at an initial current level that approximates a typical threshold-Neural Response Telemetry (NRT) level, receive an NRT measurement of neural activity within the target neural region in response to the stimulation; and a machine-learned expert system configured with a decision tree that includes at least two levels of nodes which consider parameters relating to the NRT measurement, respectively, and configured to predict, based on one or more features of the neural activity, whether the NRT measurement includes a neural response or does not include a neural response

BRIEF DESCRIPTION OF THE DRAWINGS

FIG. 1A is a graph illustrating exemplary measurements obtained of neural responses evoked by varying stimulus levels.

FIG. 1B is a graph illustrating exemplary measurements of neural response showing stimulus artifact and noise.

FIG. 4A is a high-level flow chart in accordance with one embodiment of the present invention.

FIG. 7 is a flowchart illustrating an automated algorithm for optimization of a third phase compensatory stimulus in accordance with one embodiment of the present invention.

DESCRIPTION OF EXAMPLE EMBODIMENTS

Overview

The present invention is directed to automatically analyzing an evoked neural response to determine the threshold Neural Response Telemetry (T-NRT) while avoiding the above and other drawbacks of conventional approaches. Generally, the systems, methods, techniques and approaches of the present invention apply electrical stimulation to a target neural region at incrementally greater current levels beginning with an initial current level that is as close as possible to a typical T-NRT level; record an NRT measurement of an auditory signal which generated by the target neural region in response to the stimulation; and utilize a machine-learned expert system to predict whether the NRT measurement contains a neural response based on a plurality of features extracted from the auditory signal.

In one embodiment, the initial current level is selected to insure safety while minimizing the quantity of measurements required to determine the T-NRT. As such, in post-operative applications, the initial current level is substantially below the typical T-NRT and at a current level at which a neural response is not expected to be evoked while in intraoperative applications, the initial current level is below but close to the typical T-NRT. Where it is evaluated by the decision tree that a neural response has not been evoked, the amplitude or current level of the neural stimulus is preferably incremented and the method repeated. Such embodiments provide for the amplitude or current level of the applied stimuli to be gradually increased until the expert system evaluates that a neural response has been evoked. The threshold is then locally established, preferably at a finer stimulus resolution.

Advantageously, the present invention does not require making recordings at supra-threshold stimulation levels; that is, the T-NRT values are obtained at a stimulation current level that rarely exceeds the recipient's maximum comfortable level of stimulation. Rather, embodiments of the present invention approach threshold from about the same stimulation levels and stop as soon as a confident neural response is established.

Another advantage of the present invention is the use of an expert system that considered a variety of extracted features. This is in contrast to the known conventional systems in which measurement of the neural response requires an expert operator to provide an assessment of the obtained neural response measurement based on both audiological skills and cumulative experience in interpretation of specific neural response measurements. In contrast, the present invention analyzes the measured neural responses automatically and accurately without the contribution of an expert user.

Before describing the features of the present invention, it is appropriate to briefly describe the construction of a cochlear implant system with reference to FIG. 1.

Figure 2:
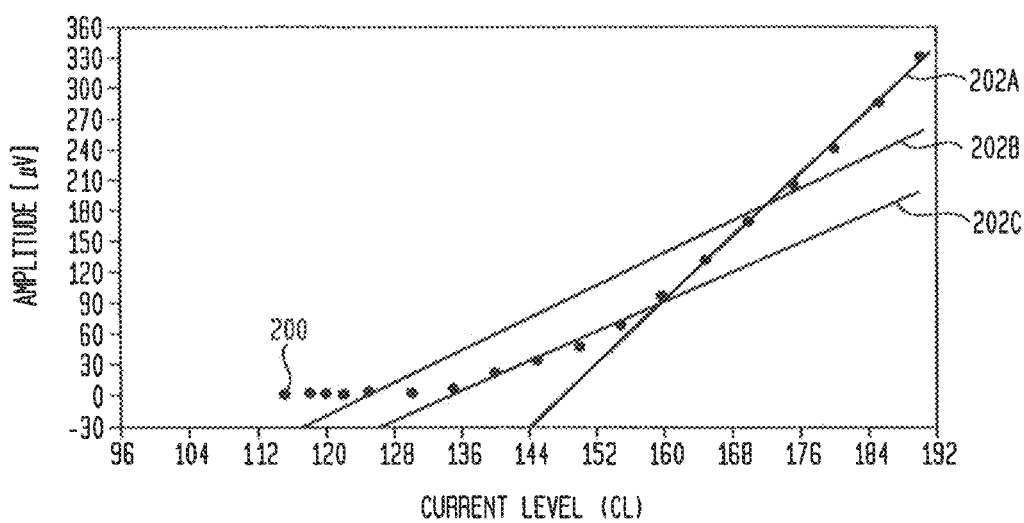
FIG. 2 is a graph of peak-to-peak evoked neural response amplitude vs. stimulus current level, showing possible regression lines.
Figure 3:
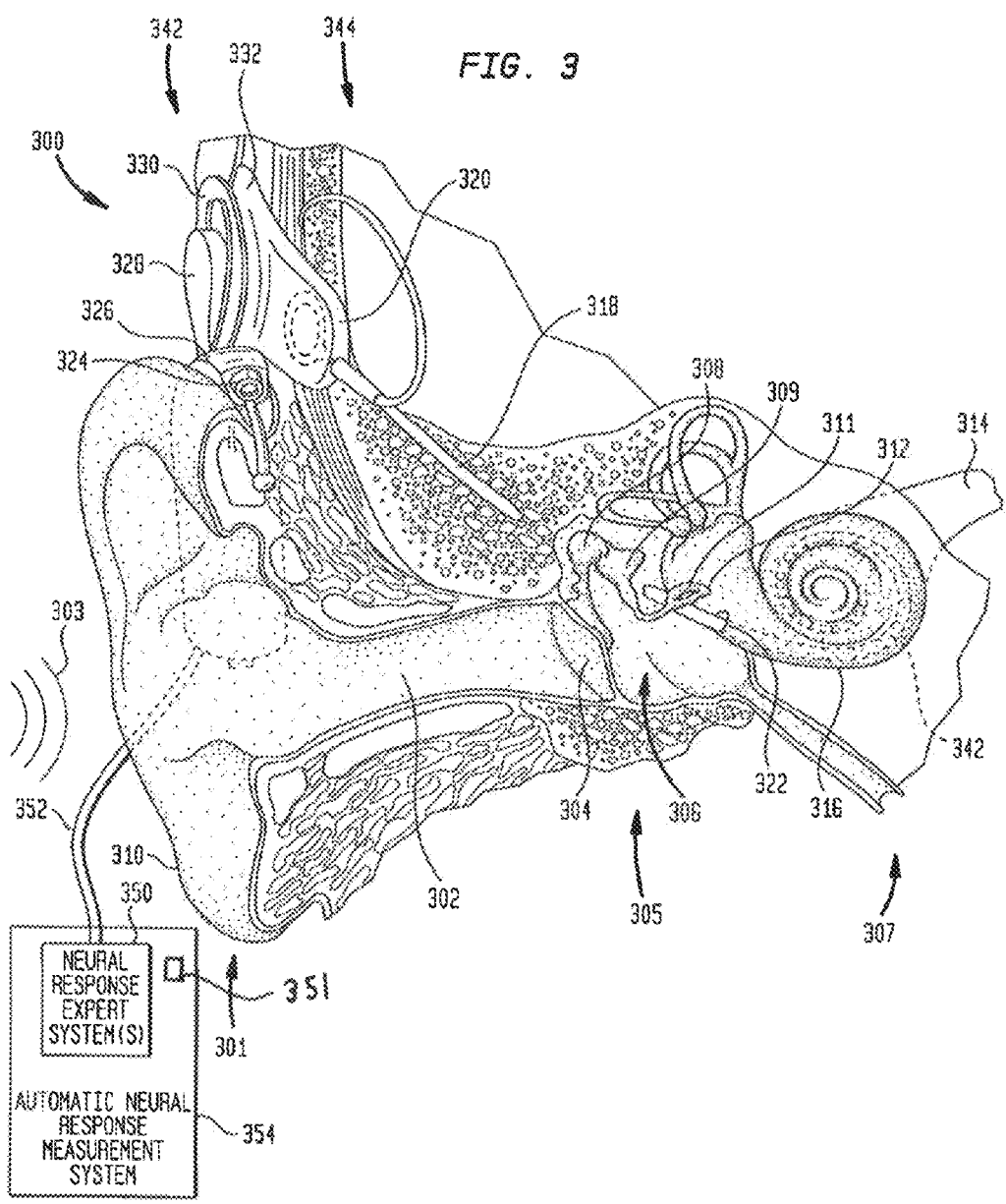
FIG. 3 is a perspective view of a cochlear implant system including a cochlear implant coupled to an expert system in which embodiments of the present invention are advantageously implemented.

FIG. 3 is a pictorial representation of a cochlear implant system in accordance with one embodiment of the present invention. Cochlear implant system 300 comprises a cochlear implant coupled to an automatic neural response measurement system in which embodiments of the present invention are advantageously implemented.

Referring to FIG. 3, the relevant components of outer ear 301, middle ear 305 and inner ear 307 are described next below. In a fully functional ear outer ear 301 comprises an auricle 310 and an ear canal 302. An acoustic pressure or sound wave 303 is collected by auricle 310 and channeled into and through ear canal 302. Disposed across the distal end of ear cannel 302 is a tympanic membrane 304 which vibrates in response to acoustic wave 303. This vibration is coupled to oval window or fenestra ovalis 312 through three bones of middle ear 305, collectively referred to as the ossicles 306 and comprising the malleus 308, the incus 309 and the stapes 311. Bones 308, 309 and 311 of middle ear 305 serve to filter and amplify acoustic wave 303, causing oval window 312 to articulate, or vibrate. Such vibration sets up waves of fluid motion within cochlea 316. Such fluid motion, in turn, activates tiny hair cells (not shown) that line the inside of cochlea 316. Activation of the hair cells causes appropriate nerve impulses to be transferred through the spiral ganglion cells and auditory nerve 314 to the brain (not shown), where they are perceived as sound.

Conventional cochlear implant system 300 comprises external component assembly 342 which is directly or indirectly attached to the body of the recipient, and an internal component assembly 344 which is temporarily or permanently implanted in the recipient. External assembly 342 typically comprises microphone 324 for detecting sound, a speech processing unit 326, a power source (not shown), and an external transmitter unit 328. External transmitter unit 328 comprises an external coil 330 and, preferably, a magnet (not shown) secured directly or indirectly to the external coil. Speech processing unit 326 processes the output of audio pickup devices 324 that are positioned, in the depicted embodiment, by ear 310 of the recipient. Speech processing unit 326 generates coded signals, referred to herein as a stimulation data signals, which are provided to external transmitter unit 328 via a cable (not shown). Speech processing unit 326 is, in this illustration, constructed and arranged so that it can fit behind the outer ear 310. Alternative versions may be worn on the body or it may be possible to provide a fully implantable system which incorporates the speech processor and/or microphone into the implanted stimulator unit.

Internal components 344 comprise an internal receiver unit 332, a stimulator unit 320, and an electrode assembly 318. Internal receiver unit 332 comprises an internal transcutaneous transfer coil (not shown), and preferably, a magnet (also not shown) fixed relative to the internal coil. Internal receiver unit 332 and stimulator unit 320 are hermetically sealed within a biocompatible housing. The internal coil receives power and data from external coil 330, as noted above. A cable or lead of electrode assembly 318 extends from stimulator unit 320 to cochlea 316 and terminates in an array of electrodes 342. Signals generated by stimulator unit 320 are applied by electrodes 342 to cochlea 316, thereby stimulating the auditory nerve 314.

In one embodiment, external coil 330 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, implantable receiver unit 332 may be positioned in a recess of the temporal bone adjacent ear 310 of the recipient.

Further details of a convention cochlear implant device may be found in U.S. Pat. Nos. 4,532,930, 6,537,200, 6,565,503, 6,575,894 and 6,697,674, which are hereby incorporated by reference herein in their entirety.

Speech processing unit 326 of cochlear implant system 300 performs an audio spectral analysis of acoustic signals 303 and outputs channel amplitude levels. Speech processing unit 326 can also sort the outputs in order of magnitude, or flag the spectral maxima as used in the SPEAK strategy developed by Cochlear Ltd.

The CI24M and CI24R model cochlear implants commercially available from Cochlear Ltd are built around the CIC3 Cochlear Implant Chip. The CI24RE cochlear implant, also commercially available from Cochlear Ltd, is built around the CIC4 Cochlear Implant Chip. Cochlear implants based on either the CIC3 or CIC4 Cochlear Implant Chip allow the recording of neural activity within cochlea 316 in response to electrical stimulation by the electrodes 342. Such Neural Response Telemetry (NRT) provides measurements of the Electrically-evoked Compound Action Potentials (ECAPs) from within cochlea 316. Generally, the neural response resulting from a stimulus presented at one electrode 342 is measured at a neighboring electrode 342, although this need not be the case.

As shown in FIG. 3, an automatic neural response measurement system 354 is communicably coupled to speech processor 326 via a cable 352. System 354 is, in one embodiment, a processor-based system such as a personal computer, server, workstation or the like, having one or more processors 351 that execute software programs to perform the infra-threshold neural response measurements of the present invention. In addition, system 354 comprises neural response expert system(s) 350 that provide neural response threshold predictions in accordance with the teachings of the present invention.

An expert system 350 is a method of solving pattern recognition problems, based on classifications performed by a human expert of the pattern domain. By presenting a sample set of patterns and their corresponding expert classifications to an appropriate computer algorithm or statistical process, systems of various descriptions can be produced to perform the recognition task. In preferred embodiments of the present invention the expert system comprises a machine learning algorithm such as the induction of decision trees.

As one of ordinary skill in the art would appreciate, expert system(s) 350 may be implemented in an external system such as system 354 illustrated in FIG. 3. In alternative embodiments, expert systems 350 may be implemented in speech processor 326 or in an implanted component of a partially or totally-implanted cochlear implant.

Figure 4B:
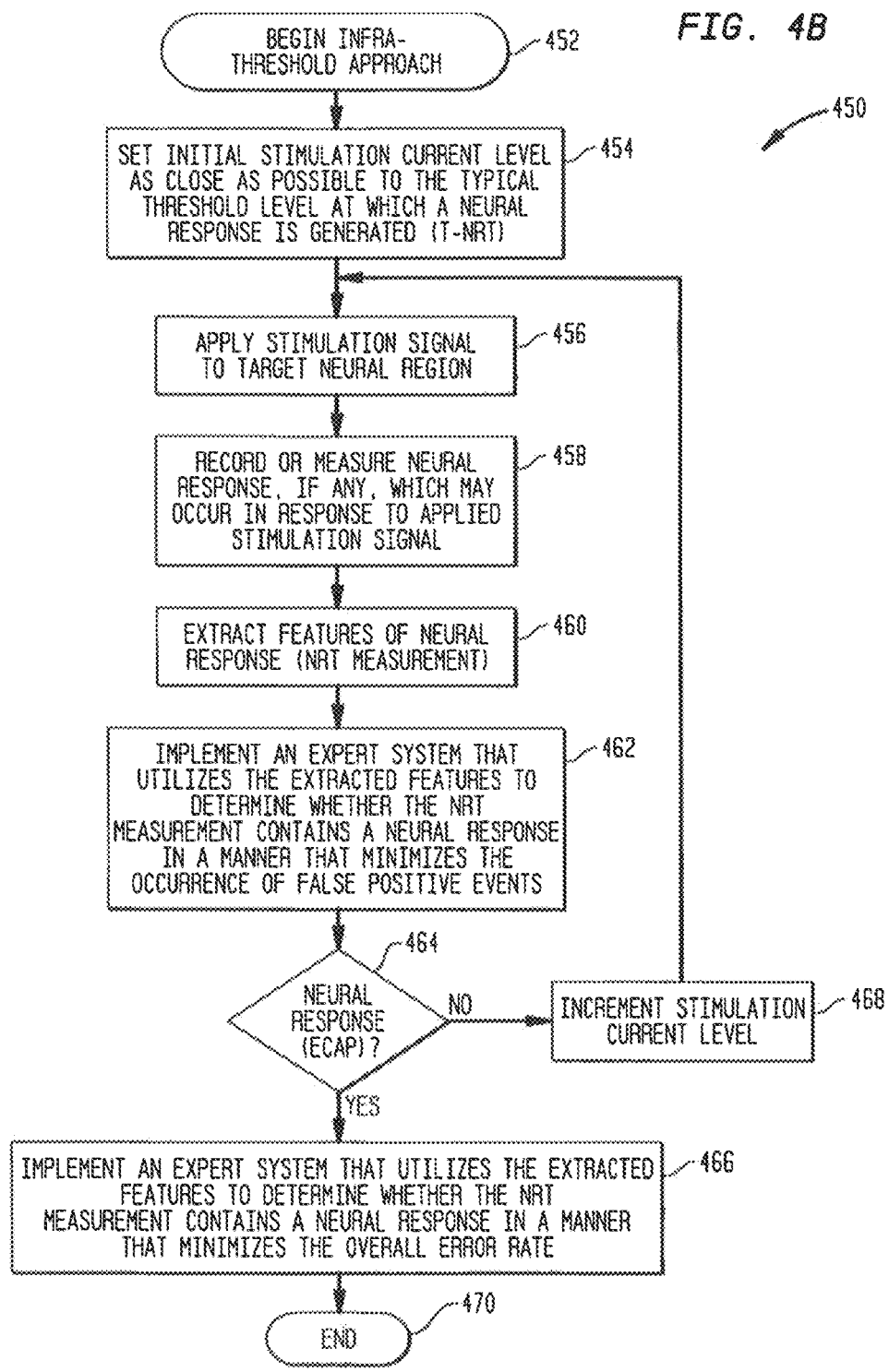
FIG. 4B is a high-level flow chart in accordance with an alternative embodiment of the present invention.

FIGS. 4A and 4B are high-level flow charts of embodiments of the present invention. Referring first to FIG. 4A, infra-threshold process 400 begins at block 402. At block 404 the initial stimulus current level is set to a level which is as close as possible to a typical threshold current level which would cause a neural response to occur. As noted, the initial current level varies with the anticipated environment (post-operative or intra-operative) and is also sufficiently high to minimize the number of NRT measurements which are to be performed. In post-operative applications the initial current level is below the anticipated T-NRT level while in intra-operative embodiments, the initial current level is above or below the anticipated T-NRT level.

At block 406 the stimulation signal is applied to the target neural region and, at block 408 the neural response is measured or recorded. During and/or subsequent to the recording of the NRT measurement, a plurality of features are extracted from the NRT measurement at block 410.

At block 412 an expert system is implemented to determine whether the NRT measurement contains a neural response. The expert system utilizes a plurality of the extracted features to make such a determination as described herein. If a neural response has not occurred (block 414) the stimulus current level is increased and the above operations are repeated. Otherwise, process 400 ceases at block 416.

In some embodiments, to avoid false positives, the amplitude or current level of the neural stimulus is preferably successively incremented until two consecutive neural stimuli have been applied both of which lead to an evaluation by the expert system that a neural response has been evoked. In such embodiments, the stimulus current level at which the first such neural response was evoked may be defined as a first minimum stimulus threshold. In such embodiments, the current level of an applied stimulus is preferably incrementally reduced from the first minimum stimulus threshold, until two consecutive stimuli have been applied both of which lead to an evaluation by the expert system that a neural response has not been evoked. The higher of such stimuli current levels at which the neural response has not been evoked is preferably defined as a second minimum stimulus threshold. Such an embodiment is illustrated in FIG. 4B, in which a second expert system is implemented to determine whether the NRT measurements taken during the descending increments contains a neural response. In one preferred embodiment, the second expert system is configured to minimize the overall error rate as compared to the first expert system which may be configured to minimize the occurrence of false positive events.

Such embodiments provide for the minimum stimulus threshold to be defined with reference to the first minimum stimulus threshold and the second minimum stimulus threshold. For example, the minimum stimulus threshold may be defined to be a current level closest to the average of the first minimum stimulus threshold and the second minimum stimulus threshold. Alternately, in embodiments where the amplitude or current level of the neural stimulus is successively incremented until two consecutive neural stimuli have been applied both of which lead to an evaluation by the decision tree that a neural response has been evoked, the minimum stimulus threshold may simply be defined to be equal to the stimulus current level at which the first such neural response was evoked.

Figure 5A:
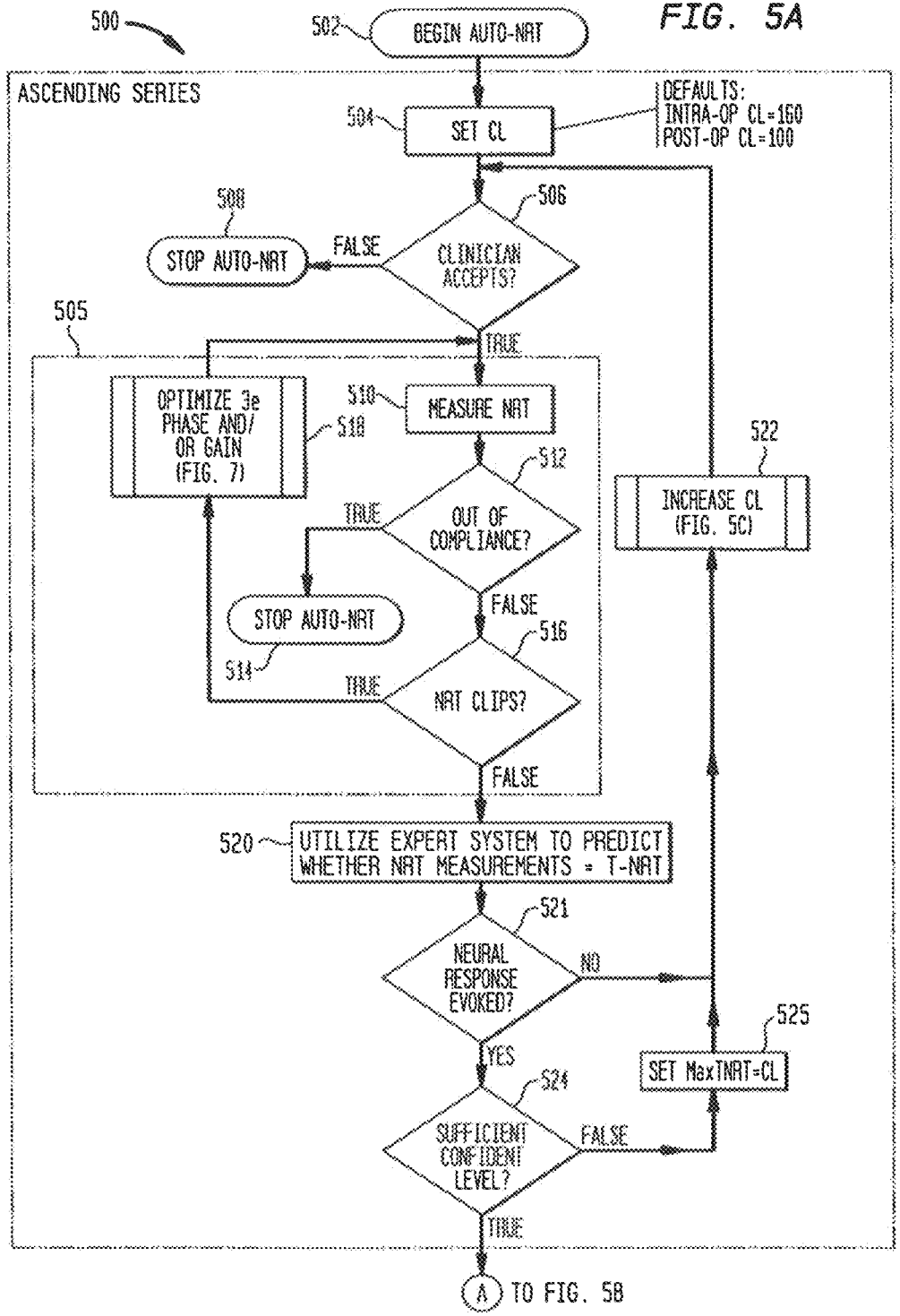
FIGS. 5A and 5B are a flowchart showing an algorithm by which a minimum stimulus threshold may be determined in accordance with an embodiment of the invention.

FIG. 5A is a flowchart illustrating the primary operations performed in one embodiment of the present invention. In this exemplary embodiment, the T-NRT level of a single electrode is measured.

Process 500 commences at block 502 and at bock 504 a stimulus current level (CL) is initialized. To insure safety of the recipient, in post-operative environments the initial current level is preferably a low value at which a neural response is not expected to be evoked. Specifically, the initial current level is set to a value that is significantly below a typical threshold level (T-NRT). In one exemplary embodiment, the initial current level is set to 100 post-operatively. However, in intra-operative environments, the noted safety concerns are not applicable due to the lack of auditory response. As such, the initial current level is set to a value that is below the typical threshold level (T-NRT). In one exemplary embodiment, the initial current level is set to 160 intra-operatively. In both environments, however, the initial current level is not set to a value unnecessarily below the typical threshold level as to do so would increase the number of NRT measurements that will be performed to reach the threshold level which causes a neural response. It should also be appreciated that the initial current level may have other values in alternative embodiments. Further, in alternative embodiments, the current level is user defined.

At block 506, a clinician is asked to accept the present value of the stimulus current level. The clinician may, for example, refuse if process 500 is being applied post-operatively and the present value of the stimulus current level would exceed a recipient's comfort threshold. Refusal causes process 500 to cease at block 508. Additionally or alternatively, process 500 may be halted to avoid a violation of electrical capabilities of the components applying the neural stimulus.

Alternatively, clinician acceptance at block 506 leads to an NRT measurement being performed at block 510. The NRT measurement performed at block 510 involves application of a stimulus at the accepted stimulus current level by at least one electrode of interest. Preferably, system 354 implements a technique that removes or minimizes stimulus artifacts. For example, in one embodiment, system 354 implements a technique similar to that described in U.S. Pat. No. 5,758,651, which is hereby incorporated by reference herein. This patent describes one conventional apparatus for recovering ECAP data from a cochlear implant. This system measures the neural response to the electrical stimulation by using the stimulus array to not only apply the stimulation but to also detect and receive the response. In this system the array used to stimulate and collect information is a standard implanted intra-cochlear and/or extra-cochlear electrode array. Following the delivery of a stimulation pulse via chosen stimulus electrodes, all electrodes of the array are open circuited for a period of time prior to and during measurement of the induced neural response. Open circuiting all electrodes during this period is to reduce the detected stimulus artifact measured with the ECAP nerve response.

In an alternative embodiment, system 354 generates a compensatory stimulus signal in a manner such as that described in WO 2602/082982 and/or WO 2004/021885, each of which is hereby incorporated by reference herein. Following application of a first stimulus to a nerve, WO 2002/082982 teaches application of a compensatory stimulus closely afterwards to counteract a stimulus artifact caused by the first stimulus. In some such embodiments, automatic optimization of the compensatory stimulus is performed thereby providing automated cancellation or minimization of stimulus artifacts from measurements of the evoked neural response.

WO 2004/021885 relates to the control of a reference voltage of a neural response amplifier throughout signal acquisition to avoid the amplifier entering saturation. While variation of the reference voltage causes the output of the amplifier to be a piecewise signal, such a piecewise signal is easily reconstructed, and thus this disclosure allows an amplifier of high gain to be used to improve signal acquisition resolution. In some such embodiments, a reference voltage of an amplifier used in the measurement process is altered during the measurement in order to produce a piecewise signal which avoids saturation of the amplifier.

A neural response to such a stimulus is measured or recorded by way of an adjacent electrode and a high gain amplifier (not shown), to yield a data set of 32 voltage samples (not shown) which form the NRT measurement (also referred to as the NRT measurement waveform or trace herein).

Operations depicted in dashed block 505 are next performed to improve recording quality and, if the quality is poor, to cease recording the neural response at that electrode. At block 512, process 500 performs a voltage level compliance check to determine whether the implant can deliver the required stimulus current by providing sufficient electrode voltage. If the compliance check determines that that an error has occurred, such as by reading a flag generated by the above-noted sound processor chips, cause process 500 ceases at block 514. However, if at block 512 it is determined that the hardware is in compliance, processing continues at block 516:

At block 516 a check is made of whether clipping of the NRT amplifier occurred. In one embodiment, this too may be determined by reading a Boolean flag generated by the above-noted sound processing chips. If NRT amplifier clipping occurred, then processing continues at block 518 at which the compensatory stimulus and/or the amplifier gain is optimized. The operations performed at block 518 are described in detail below with reference to FIG. 7. Processing then returns to block 510 and the above operations are repeated.

At block 520, a machine-learned expert system is utilized to predict whether an NRT measurement contains a neural response based on the plurality of extracted auditory signal features. In one embodiment, the expert system was built using the induction of decision trees. In one implementation of such an embodiment, the induction of decision trees machine learning algorithm is the algorithm C5.0 described in Quinlan, J., 1993. "C4.5: Programs for Machine Learning." Morgan Kaufmann, San Mateo; and Quinlan, J., 2004. "See5: An Informal Tutorial." Rulequest Research, both of which are hereby incorporated by reference herein.

Figure 6A:
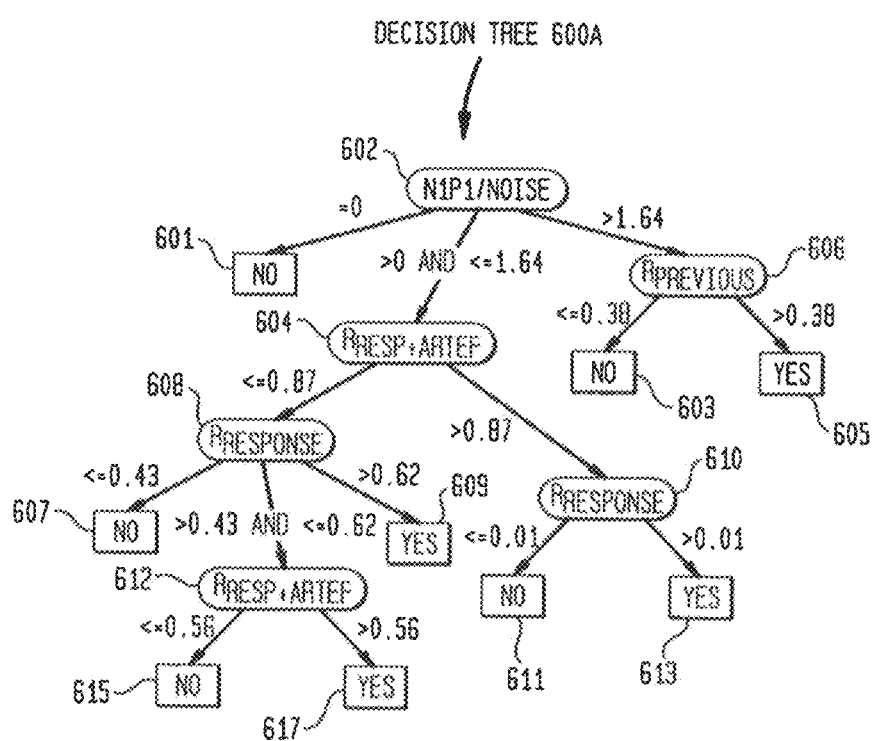
FIG. 6A illustrates one embodiment of a decision tree used in the embodiment of FIG. 5A to determine whether a neural response has been evoked.

In one embodiment, the decision tree 600A illustrated in FIG. 6A is applied to the obtained 32 sample set measurement of the NRT measurement. That is, neural response expert system 350 considers or processes a plurality of features extracted from the NRT measurement to determine if it contains a "good" neural response. As used herein, a "good" neural response is one which approximates a true neural response to the applied stimulus level as determined by a sampling a statistically-significant population of recipients.

Should decision tree 600A determine that a given NRT measurement does not contain a "good" neural response and thus that a neural response has not been evoked (block 521), the process 500 continues at block 522 at which the stimulus current level CL is incrementally increased. The operations performed at block 522 are described below with reference to FIG. 5C. Process 500 then proceeds to block 506 and the above operations are repeated using this higher current level.

Should process 500 determine at block 521 that a neural response has been evoked, then at block 524 an assessment is made as to whether there is confidence in this determination. There are many ways to evaluate the confidence of the prediction made by the expert system operating at block 520. In one exemplary embodiment, process 500 determines at block 524 whether two consecutive stimuli have each evoked a neural response. If not, a variable 'MaxT-NRT' is set at block 525 to the applied stimulus current level for use at block 522. Process 500 then proceeds to block 522 as shown in FIG. 5A. If two consecutive stimuli have each evoked a neural response, the process 500 continues with operations depicted in FIG. 5B to accurately determine the minimum threshold stimulation current which causes a neural response. These operations are described in detail below with reference to FIG. 5B.

Figure 5B:
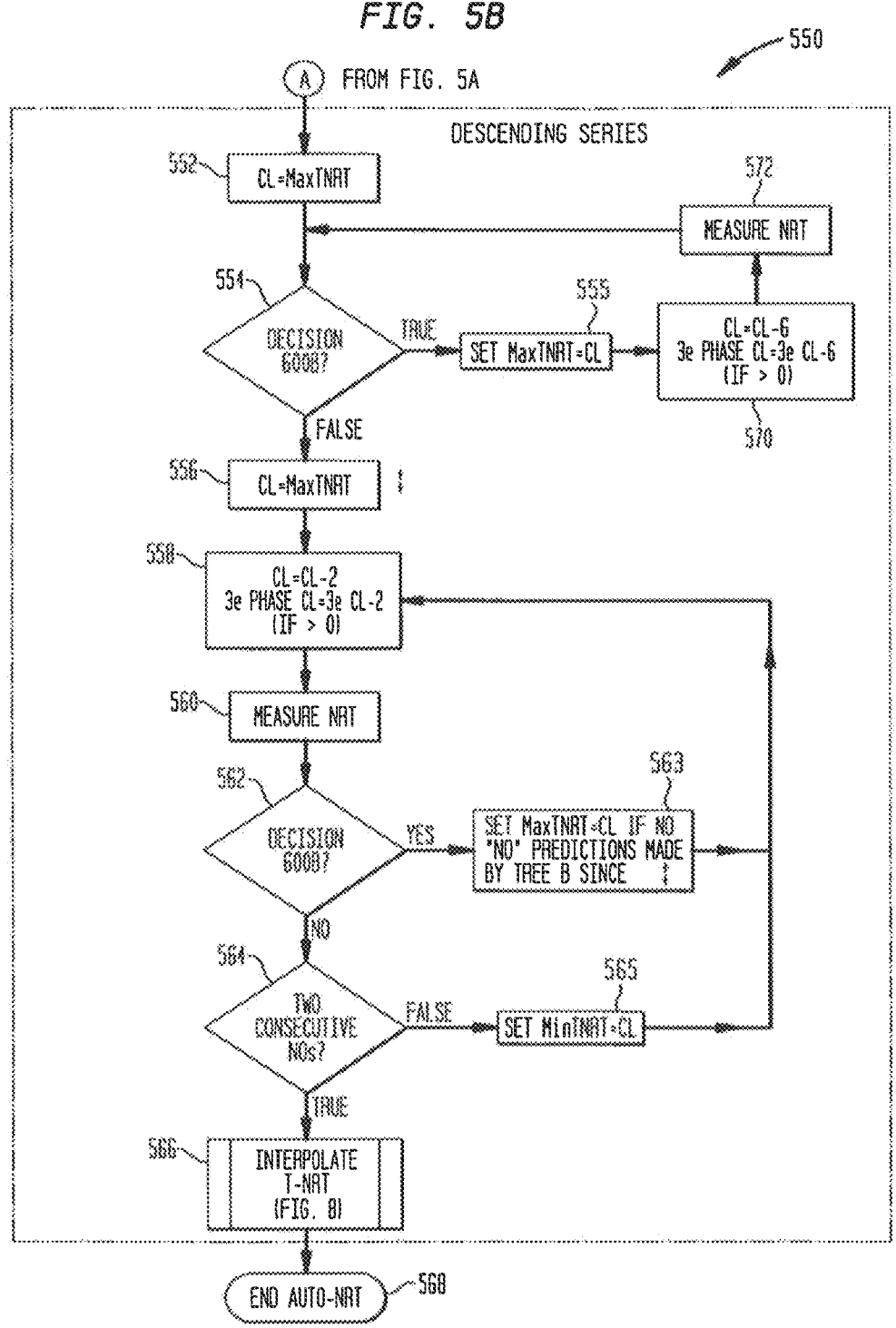
Figure 5C:
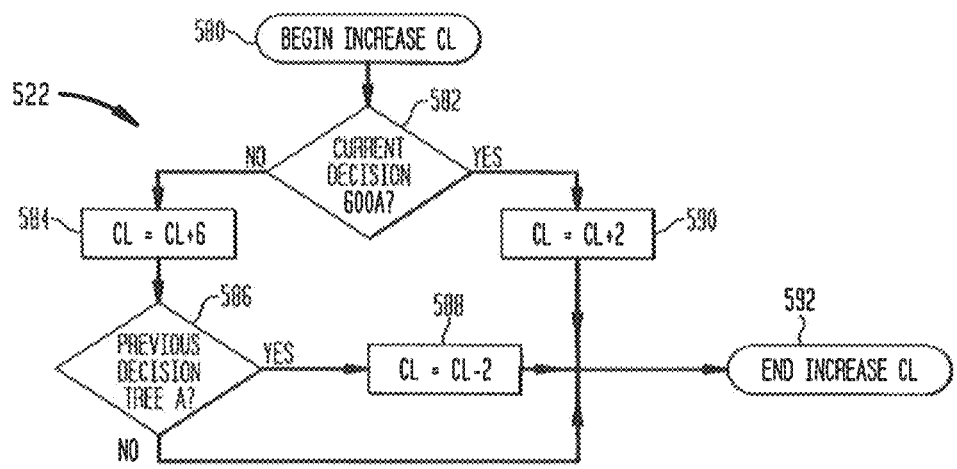
FIG. 5C is a flowchart showing an algorithm by which the stimulus current level is incremented in accordance with an embodiment of the invention.

Referring now to FIG. 5C, the operations performed at block 522 in one embodiment of the present invention are described next below. The size of the increment in the value of the stimulus current level depends on the following decision tree predictions:

6 current level units if both the present and previous NRT measurements are not deemed a neural response (blocks 582, 584 and 586).
 4 current level units if the present NRT measurement is not deemed a neural response whereas the previous measurement was predicted otherwise (blocks 582, 586, 588).
 2 current level units if the present NRT measurement is deemed a neural response (blocks 582, 590).

If at block 524 it is determined that the T-NRT has been predicted with sufficient confidence, then process 500 continues with the descending series of operations illustrated in FIG. 5B. In the exemplary embodiment, an acceptable confidence level is attained if two consecutive stimuli have each evoked a neural response. When that occurs, the stimulus current level is reset to be equal to MaxT-NRT at block 552.

Figure 6B:
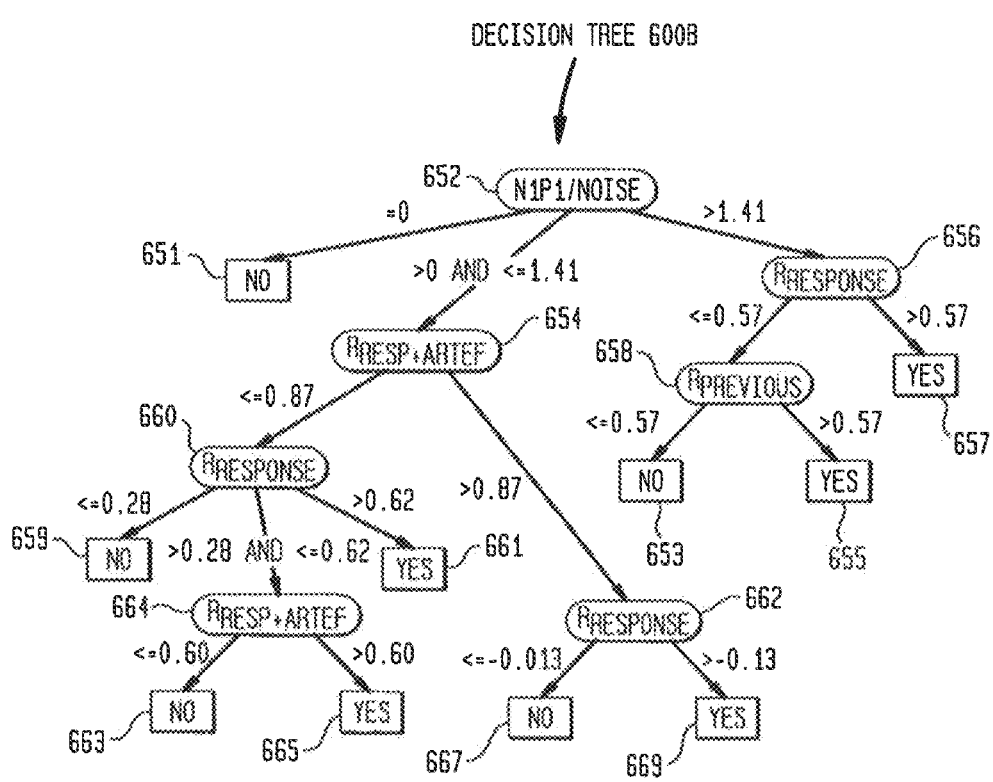
FIG. 6B illustrates one embodiment of a decision tree used in the embodiment of FIG. 5B to determine whether a neural response has been evoked.

At block 554, a decision tree 600B, depicted in FIG. 6B, is applied to the latest 32 sample set measurement of the neural response. Should decision tree 600B determine that a neural response has been evoked, MaxT-NRT is set to the present stimulus current level value at block 555. The stimulus current level is then decremented by 6 current level units at block 580. This increment size may be another value or user definable in alternate embodiments.

In one preferred embodiment, separate decision trees 600A and 600B are used for various phases of process 500. As described above, decision tree 600A is used in the ascending phase illustrated in FIG. 5A, and is optimized for a low false positive rate. Decision tree 600B, on the other hand, is used in the descending phase of process 500 illustrated in FIG. 5B, and is optimized for a low overall error rate.

At block 572 an NRT measurement is made in the same manner as that performed at block 510, and process 500 returns to block 554. Should decision tree 600B determine that a neural response has not been evoked, the stimulus current level is reset to MaxT-NRT at block 556.

At block 558, the current level is decremented by 2 current level units, which is a smaller interval than the increment applied at block 522, and the decrement applied at block 530.

At block 560, an NRT measurement is again performed during the CL decrementing stage, in the same manner as the NRT measurement performed at block 510.

At block 562 the decision tree 600B is again applied to the obtained 32-sample NRT measurement, in order to determine whether a neural response has been evoked by application of the stimulus at the present current level. If so, the algorithm returns to step 558. At block 563 MaxT-NRT is set to the present value of the stimulus current level if decision tree 600B has always deemed that a neural response has been evoked since block 556.

If decision tree 600B determines that a neural response has not been evoked, then at block 564 a determination is made as to whether two consecutive stimuli have not evoked a neural response. If there have not been two consecutive stimuli which have not evoked a neural response, a variable 'MinT-NRT' is set to be equal to the present value of CL, and process 500 returns to block 558. If there has been two consecutive stimuli which have not evoked a neural response, then at block 566 a T-NRT value is determined from the two variables of MaxT-NRT and MinT-NRT, in the manner described below with reference to FIG. 8. Process 500 then ceases at block 568.

If the current level of any stimulation pulse [probe, masker, etc.] ever exceeds its range, the measurement is stopped.

In one embodiment, the algorithm is further optimized such that no NRT measurement is repeated at a given current level throughout the algorithm. Previous measurements may be used if they exist for the required current level.

FIG. 6A illustrates one embodiment of a decision tree used in the embodiment of FIG. 5A to determine whether a neural response has been evoked. FIG. 6B illustrates one embodiment of a decision tree used in the embodiment of FIG. 5B to determine whether a neural response has been evoked. The utilization of two decision trees 600A and 600B to determine T-NRT is advantageous is some applications. In the flowchart illustrated in FIG. 5A, the stimulation current level is incrementally increased and T-NRT has not yet been predicted. In such a process, decision tree 600A is utilized to provide a low false-positive rate so that a neural response can be predicted with a high degree of confidence. Thereafter, while descending at finer increments in the flowchart illustrated in FIG. 5B, decision tree 600B is utilized due to its ability to more accurately predict a neural response has occurred.

Each parameter considered in decision tree structure or dichotomous key 600A is defined herein below. As one of ordinary skill in the art would appreciate, the use of the terms attributes, parameters, features and the like are commonly used interchangeably to refer to the raw and calculated values utilized in a decision tree. The selection of such terms herein, then, is solely to facilitate understanding. It should also be appreciated that the first occurring peak positive and negative values of an NRT measurement waveform are commonly referred to as P1 and N1, respectively, as noted above. For ease of description, these terms are utilized below. In the following description, the parameters considered at each of the decision nodes 602, 604, 606, 608, 610 and 612 are first described followed by a description of decision tree 600A.

Parameter N1P1/Noise is considered at decision node 602. Parameter N1P1/Noise represents the signal to noise ratio of the NRT measurement. As noted, in the exemplary embodiment, each NRT measurement provides a trace or waveform derived from 32 samples of the neural response obtained at a sampling rate of 20 kHz.

N1 is the minimum of the first 8 samples.

P1 is the maximum of the samples after N1, up to and including sample 16.

N1−P1 (µV)=$ECAP_{P1}-ECAP_{N1}$

If any of the following rules are true, N1−P1=0:
  N1−P1<0
  Latency between N1 and P1<2 samples
  Latency between N1 and P1>12 samples
  Latency between N1 and the maximum sample post-N1>15 samples AND Ratio of N1−P1 to the range N1 onwards <0.85

Noise=the range (maximum minus minimum) of samples 17-32.

N1P1/Noise=N1−P1 (amplitude) divided by Noise (the noise level).

Figure 9:
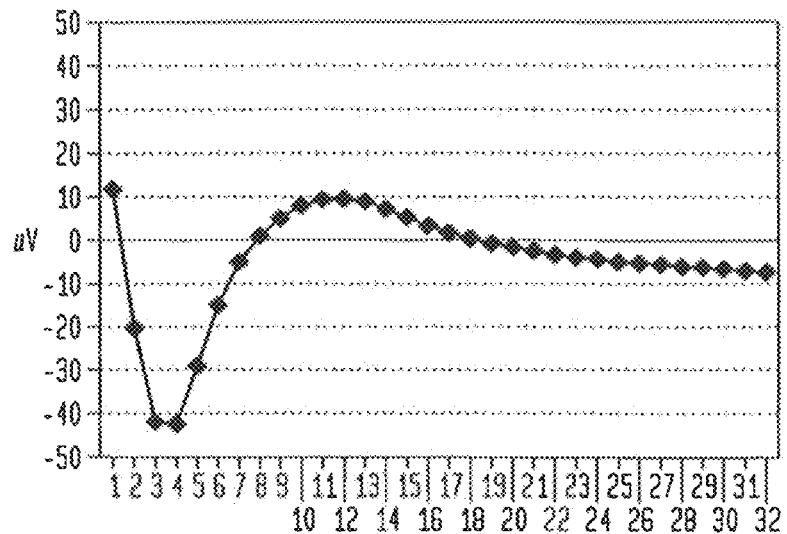
FIG. 9 is a graph illustrating a predefined expected or 'good' neural response used for comparison by a portion of the decision tree of FIG. 6.

Parameter $R_{Response}$ is considered at decision nodes 608 and 610. Parameter $R_{Response}$ is defined as the correlation coefficient between the given NRT measurement and a fixed good response, calculated over samples 1-24. A predefined 32 sample standard response used in the present embodiment is shown in FIG. 9. In this embodiment, the standard correlation coefficient is utilized:

$$r = \frac{\sum_{Samples}(x-\bar{x})(y-\bar{y})}{\sqrt{\sum_{Samples}(x-\bar{x})^2 \sum_{Samples}(y-\bar{y})^2}}$$

Figure 10:
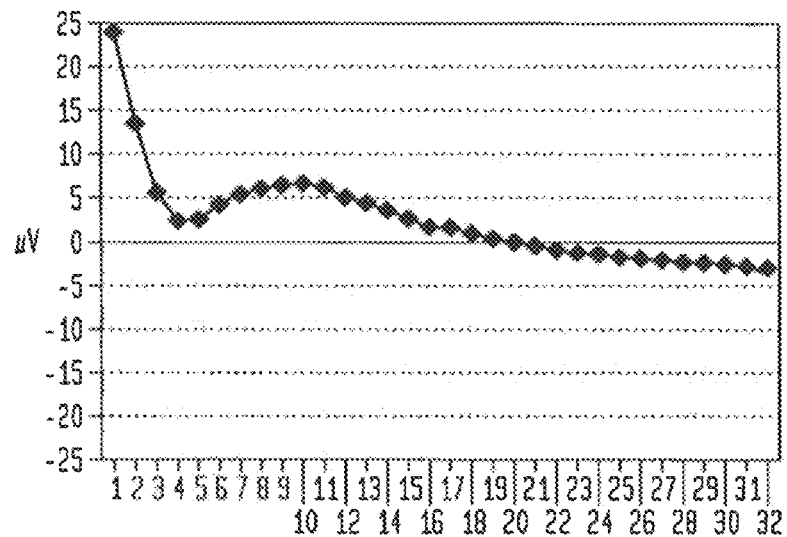
FIG. 10 is a graph illustrating a predefined expected or 'good' neural response plus stimulus artifact used for comparison by a portion of the decision tree of FIG. 6.
Figure 11:
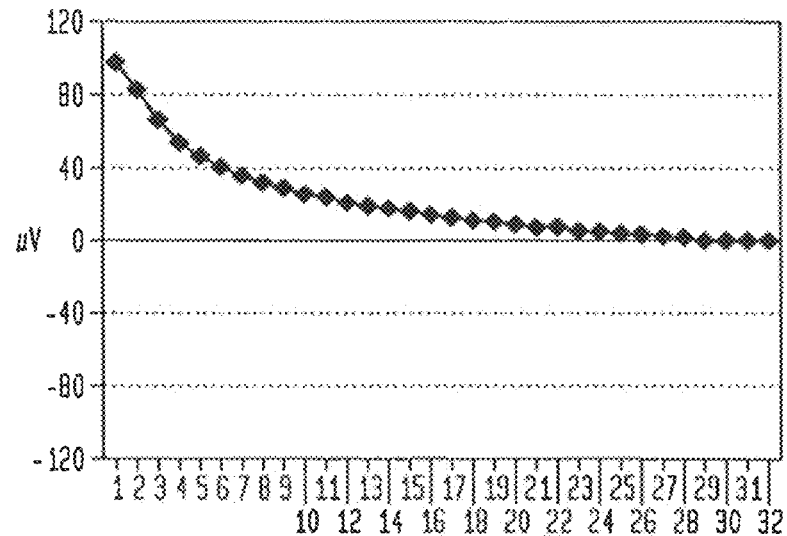
FIG. 11 illustrates a predefined expected or 'good' stimulus artifact.

Parameter $R_{Resp+Artef}$ is considered a decision nodes 604 and 612. Parameter $R_{Resp+Artef}$ is defined as the correlation coefficient between the given NRT measurement and a fixed trace with neural response plus artifact, calculated over samples 1-24. A predefined 32 sample standard response used in the present embodiment is shown in FIG. 10.

Parameter $R_{Previous}$ is considered a decision node 606. Parameter $R_{Previous}$ is defined as the correlation coefficient between the given NRT measurement and the NRT of measurement of immediately lower stimulus current level, calculated over samples 1-24. In one embodiment, any previously performed measurement of lower stimulus level, whether the step difference is 2CL, 6CL, etc.

As shown in FIG. 6A, when N1P1/Noise is zero, decision tree 600A predicts that the NRT measurement does not contain a neural response as illustrated by decision node 601. Should N1P1/Noise 602 have a value between 0.0 and 1.64, then the value of parameter $R_{Resp+Artef}$ is considered at decision node 604. Similarly, should N1P1/Noise have a value greater than 1.64, then the value of parameter $R_{Previous}$ is considered at decision node 606.

At decision node 604 of parameter RResp+Anef is considered. If it determined to be less than or equal to 0.87, then parameter $R_{Response}$ is determined at decision node 608. However, if $R_{Resp+Artef}$ is determined to be greater than 0.87, then a different consideration of parameter $R_{Response}$ is performed at decision node 610.

Returning to decision node 606 at which parameter $R_{Previous}$ is considered. If the parameter is less than or equal to 0.38, then decision tree 600A determines that the given NRT measurement fails to contain a neural response, as indicated at block 603 of FIG. 6A. However, if the parameter is greater than 0.38, then decision tree 600A determines that the given NRT measurement does contain a neural response, as indicated at block 605 of FIG. 6A. Thus, if the parameter N1P1/Noise is greater than 1.64 and the parameter $R_{Previous}$ is greater than 0.38, then the NRT measurement is predicted to contain a neural response.

At decision node 608 decision tree 600A considered whether parameter $R_{Response}$ is less than or equal to 0.43, in which case decision tree 600A predicts that the NRT measurement does not contain a neural response, as shown at block 607. At decision node 608 decision tree 600A also considers whether parameter $R_{Response}$ is greater than 0.62, at which decision tree 600A predicts that the NRT measurement does contain a neural response, as shown at block 609. Thus, if the parameter N1P1/Noise is greater than zero and less than or equal to 1.64, parameter $R_{Resp+Artef}$ is less than or equal to 0.87 and parameter $R_{Response}$ is less than 0.62, then decision tree 600A predicts that the NRT measurement contains a neural response.

At decision node 610 decision tree 600A considered whether parameter $R_{Response}$ is less than or equal to 0.01, in which case decision tree 600A predicts that the NRT measurement does not contain a neural response, as shown at block 611. At decision node 610 decision tree 600A also considers whether parameter $R_{Response}$ is greater than 0.01, at which decision tree 600A predicts that the NRT measurement does contain a neural response, as shown at block 613. Thus, if the parameter N1P1/Noise is greater than zero and less than or equal to 1.64, parameter $R_{Resp+Artef}$ is greater than 0.87, and parameter $R_{Response}$ is greater than 0.01, then decision tree 600A predicts that the NRT measurement contains a neural response.

Returning to decision node 608, decision tree 600A also considers whether parameter $R_{Response}$ is greater than 0.43 and less than or equal to 0.62. If so, decision tree 600A considers parameter $R_{Resp+Artef}$ at decision node 612. There, if $R_{Resp+Artef}$ is less than or equal to 0.56, then decision tree 600A predicts that the NRT measurement does not contain a neural response, as indicated at block 615. Alternatively, if $R_{Resp+Artef}$ is greater than 0.56, then decision tree 600A predicts that the NRT measurement contain a neural response, as indicated at block 617. Thus, if the parameter N1P1/Noise is greater than zero and less than or equal to 1.64, parameter $R_{Resp+Artef}$ is less than or equal to 0.87, parameter $R_{Response}$ is greater than 0.43 and less than or equal to 0.62, and parameter $R_{Resp+Artef}$ is greater than 0.56, then decision tree 600A predicts that the NRT measurement contains a neural response.

As one or ordinary skill in the art would appreciate, the above values are exemplary only. For example, in one alternative embodiment, N1 is determined based on a quantity of sampled other than eight. Similarly, the positive peak occurs after the negative peak in NRT measurement waveforms. In the above embodiment, the positive peak is limited to the maximum sample after the first occurring negative peak N1. However, because the trailing portion of an NRT waveform is generally level and should not contain a pulse. It should be appreciated, however, that in alternative embodiments, P1 is defined as the maximum sample which occurs after N1 and less than 14-18 samples. Similarly, the latency between the first occurring negative and positive peaks may be other than 2 and 12 samples in alternative embodiments and so on.

Referring now to FIG. 6B, decision tree 600B will be described. The parameters or features considered or evaluated at decision blocks 652, 54, 656, 658, 660, 662 and 664 are described above.

At decision node 652 parameter NIP1/Noise is considered by decision tree 600B. If the parameter N1P1/Noise zero, decision tree 600B predicts that the NRT measurement does not contain a neural response as illustrated by decision node 651. Should the parameter N1P1/Noise have a value greater than 0.0 and less than or equal to 1.41, then the value of parameter RResp+Artef is considered at decision node 654. Similarly, should the parameter N1P1/Noise have a value greater than 1.41, then the value of parameter $R_{Response}$ is considered at decision node 656.

At decision node 654, parameter $R_{Resp+Artef}$ is considered. If this parameter determined to be less than or equal to 0.87, then parameter $R_{Response}$ is considered at decision node 660. However, if $R_{Resp+Artef}$ is determined to be greater than 0.87, then a different consideration of parameter $R_{Response}$ is performed at decision node 662.

Returning to decision node 656 at which parameter $R_{Response}$ is considered. If the parameter is less than or equal to 0.57, then decision tree 600B considers the parameter $R_{Previous}$ at decision node 658. However, if the parameter $R_{Previous}$ is greater than 0.57, then decision tree 600B determines that the given NRT measurement contains a neural response, as indicated at block 657 of FIG. 6B. Thus, if the parameter N1P1/Noise is greater than 1.41 and the parameter $R_{Response}$ is greater than 0.57, then the NRT measurement is predicted to contain a neural response.

Returning to decision node 658 at which parameter $R_{Previous}$ is considered. If this parameter is less than or equal to 0.57, then decision tree 600B determines that the given NRT measurement fails to contain a neural response, as indicated at block 663 of FIG. 6B. However, if this parameter is greater than 0.57, then decision tree 600B determines that the given NRT measurement does contain a neural response, as indicated at block 655 of FIG. 6B. Thus, if the parameter N1P1/Noise is greater than 1.41, the parameter $R_{Response}$ is less than or equal to 0.57, and the parameter $R_{Previous}$ is greater than 0.57, then the NRT measurement is predicted to contain a neural response.

At decision node 660 decision tree 600B considered whether parameter $R_{Response}$ is less than or equal to 0.28, in which case decision tree 600B predicts that the NRT measurement does not contain a neural response, as shown at block 659. At decision node 608 decision tree 600B also considers whether parameter $R_{Response}$ is greater than 0.62, in which case decision tree 600B predicts that the NRT measurement does contain a neural response, as shown at block 661. Thus, if the parameter N1P1/Noise is greater than zero and less than or equal to 1.41, parameter $R_{Resp+Artef}$ is less than or equal to 0.87, and parameter $R_{Response}$ is greater than 0.62, then decision tree 600B predicts that the NRT measurement contains a neural response.

At decision node 662 decision tree 600B considered whether parameter $R_{Response}$ is less than or equal to 0.013, in which case decision tree 600B predicts that the NRT measurement does not contain a neural response, as shown at block 667. At decision node 662 decision tree 600B also considers whether parameter $R_{Response}$ is greater than 0.013, in which case decision tree 600B predicts that the NRT measurement does contain a neural response, as shown at block 669. Thus, if the parameter N1P1/Noise is greater than zero and less than or equal to 1.41, parameter $R_{Resp+Artef}$ is greater than 0.87, and parameter $R_{Response}$ is greater than 0.013, then decision tree 600B predicts that the NRT measurement contains a neural response.

Returning to decision node 660, decision tree 600B also considers whether parameter $R_{Response}$ is greater than 0.43 and less than or equal to 0.62. If so, decision tree 600B considers parameter $R_{Resp+Artef}$ at decision node 664. There, if the parameter $R_{Resp+Artef}$ is less than or equal to 0.60, then decision tree 600B predicts that the NRT measurement does not contain a neural response, as indicated at block 663. Alternatively, if $R_{Resp+Artef}$ is greater than 0.60, then decision tree 600B predicts that the NRT measurement contains a neural response, as indicated at block 665. Thus, if the parameter N1P1/Noise is greater than zero and less than or equal to 1.41, parameter $R_{Resp+Artef}$ is less than or equal to 0.87, parameter $R_{Response}$ is greater than 0.28 and less than or equal to 0.62, and parameter $R_{Resp+Artef}$ is greater than 0.60, then decision tree 600B predicts that the NRT measurement contains a neural response.

As one or ordinary skill in the art would appreciate, the above values are exemplary only, and that other decision trees with other parameters and decision values may be implemented.

FIG. 7 is a flow chart of one embodiment of the primary operations performed to optimize the artifact reduction pulse (3e phase) and/or amplifier gain to avoid amplifier saturation in block 518 of FIG. 5A. After process 518 begins at block 702, it is initially attempted to optimize 3e phase with relaxed criteria at block 704.

If 3e phase optimization does not converge (block 706) or if amplifier clipping still occurs (block 714), and process 518 continues at decision block 710 at which the gain is measured. If the gain is greater than 40 dB, then at block 716 the gain is decreased by 10 dB and number of sweeps is increased by a factor of 1.5. On the other hand, if the gain is not greater than 40 dB (block 710), automated T-NRT is cancelled for the electrode.

The NRT is measured again at block 718 and amplifier clipping is evaluated at block 720. If amplifier clipping 720 still occurs, process 518 returns to block 704 and the above optimization process is repeated.

Returning to block 706, if the 3e phase optimization converged (block 706) and if amplifier clipping ceases (block 714), then process 518 ceases at block 722. Similarly, if at block 722 amplifier clipping ceases after the optimizations made at block 716, then operation 518 also ceases at block 722.

Figure 8:
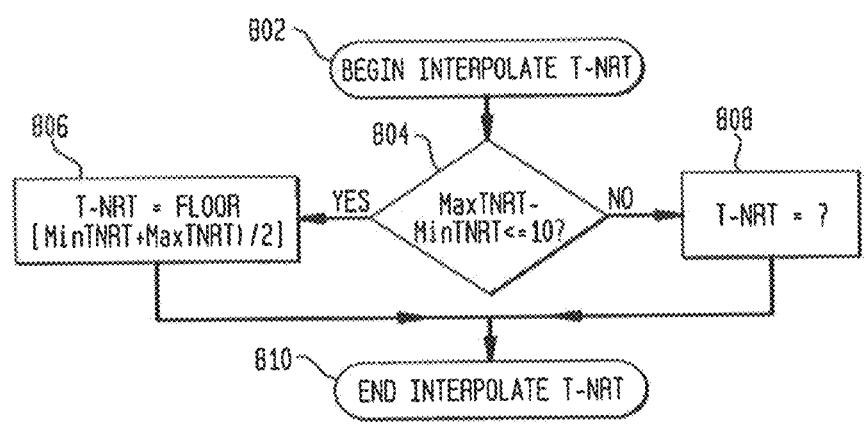
FIG. 8 is a flowchart illustrating the derivation of the minimum stimulus threshold T-NRT from MaxT-NRT and MinT-NRT values, in accordance with one embodiment of the present invention.

FIG. 8 is a flowchart illustrating the derivation of the minimum stimulus threshold T-NRT from MaxT-NRT and MinT-NRT values, in accordance with one embodiment of the present invention, introduced above with reference to block 566 of FIG. 5B. In this embodiment, the minimum T-NRT level is interpolated based on the intermediate results of the automated T-NRT measurement.

After start block 802, process 566 advances to block 804, at which the difference between the Maximum T-NRT and the minimum T-NRT is measured. If it is less than or equal to 10, then the result is deemed to be confident within ±5 current levels, and a final value is output at block 806. Otherwise, if a confident result cannot be determined by the automated T-NRT algorithm, process 566 continues at block 808 at which a "?" flag is returned.

In one embodiment, the present embodiment is implemented in automated T-NRT measurements using clinical and electrophysiological software. In alternative embodiments, the present invention is implemented in software, hardware or combination thereof.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

For example, in an alternative embodiment, a gain of the amplifier may be altered between application of successive stimuli. Such embodiments provide for automated optimization of the gain of the amplifier to maximize signal resolution while avoiding amplifier saturation.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

The above description is intended by way of example only.

What is claimed is:

1. A system communicably coupled to a cochlear implant implanted in a recipient, comprising:
   one or more processors configured to:
      cause the cochlear implant to apply electrical stimulation to a target neural region at an initial current level,
      receive a Neural Response Telemetry (NRT) measurement of neural activity evoked within the target neural region in response to the electrical stimulation; and
   a machine-learned expert system configured with a decision tree that includes at least two levels of nodes which consider parameters relating to the NRT measurement, respectively, to predict, based on one or more features of the neural activity, whether the NRT measurement includes a neural response or does not include a neural response.

2. The system of claim 1, wherein machine-learned expert system is configured to:
   evaluate at least two successive ones of the levels of nodes in order to predict whether the NRT measurement includes a neural response or does not include a neural response.

3. The system of claim 2, wherein at least one of the evaluated levels includes a node which considers a correlation coefficient relating the NRT measurement to a selected value.

4. The system of claim 1, wherein the one or more processors are configured to:
   select the initial current level to insure safety while minimizing a quantity of measurements required to determine the threshold-NRT (T-NRT) level of the target neural region.

5. The system of claim 1, wherein to select the initial current level, the one or more processors are configured to:
   select an initial current level that is below an estimated threshold-NRT (T-NRT) level.

6. The system of claim 1, wherein when the machine-learned expert system predicts that the NRT measurement does not contain a neural response, the one or more processors are configured to:
   increment the current level of the electrical stimulation to a second current level;
   cause the cochlear implant to apply electrical stimulation to a target neural region at the second current level,
   receive a second NRT measurement of neural activity within the target neural region in response to the electrical stimulation at the second current level, and
   wherein the machine-learned expert system is configured to use the decision tree to predict, based on one or more features of the neural activity within the target neural region in response to the electrical stimulation at the second current level, whether the second NRT measurement includes a neural response.

7. The system of claim 1, wherein the one or more processors:
   locally establish a threshold-NRT (T-NRT) level of the target neural region; and
   set the initial current level based on the locally established T-NRT level.

8. The system of claim 1, wherein at least one of the two levels of nodes in the decision tree considers one or more of:
   a parameter relating to the correlation of the NRT measurement to a previous measurement with neural stimulus of similar level; and
   a parameter relating to a stimulus current level.

9. The system of claim 1, wherein at least one of the two levels of nodes in the decision tree considers:
   a parameter relating to a ratio of a peak-to-peak amplitude of the NRT measurement to a noise of the measurement.

10. The system of claim 1, wherein at least one of the two levels of nodes in the decision tree considers:
    a parameter relating to a correlation of the NRT measurement to a predefined expected neural response.

11. The system of claim 1, wherein at least one of the two levels of nodes in the decision tree considers:
    a parameter relating to the correlation of the NRT measurement to a predefined expected trace containing neural response plus stimulus artifact.

12. The system of claim 1, wherein at least one of the two levels of nodes in the decision tree considers:
    a parameter relating to the correlation of the NRT measurement to a predefined expected trace containing stimulus artifact only.

* * * * *